United States Patent [19]

Blatherwick et al.

[11] Patent Number: 4,693,684

[45] Date of Patent: Sep. 15, 1987

[54] RATCHET TYPE DISPENSER FOR DENTAL MATERIALS

[75] Inventors: William J. Blatherwick, Hamilton Square; Leslie Hamilton, Trenton; Robert D. Holewinski, Lakehurst; Virginia A. Shen, East Brunswick, all of N.J.; Jeffrey Kapec, Westport; Kazuna Tanaka, Cos Cob, both of Conn.

[73] Assignee: Johnson & Johnson Dental Products Company, East Windsor, N.J.

[21] Appl. No.: 868,494

[22] Filed: May 30, 1986

[51] Int. Cl.⁴ .............................................. A61C 5/04
[52] U.S. Cl. ...................................................... 433/90

[58] Field of Search ...................................... 433/89, 90

[56] References Cited

U.S. PATENT DOCUMENTS 3,221,409 12/1965 Thiel et al. ............................ 433/90
4,479,781 10/1984 Herold et al. ........................ 433/90

Primary Examiner—Robert Peshock
Attorney, Agent, or Firm—Donal B. Tobin

[57] ABSTRACT

A ratchet-type dispenser for dental materials is disclosed. The ratchet is activated by a drive pawl and is prevented from returning by a detent pawl. The drive pawl and detent pawl are activated by the same lever arm.

3 Claims, 6 Drawing Figures

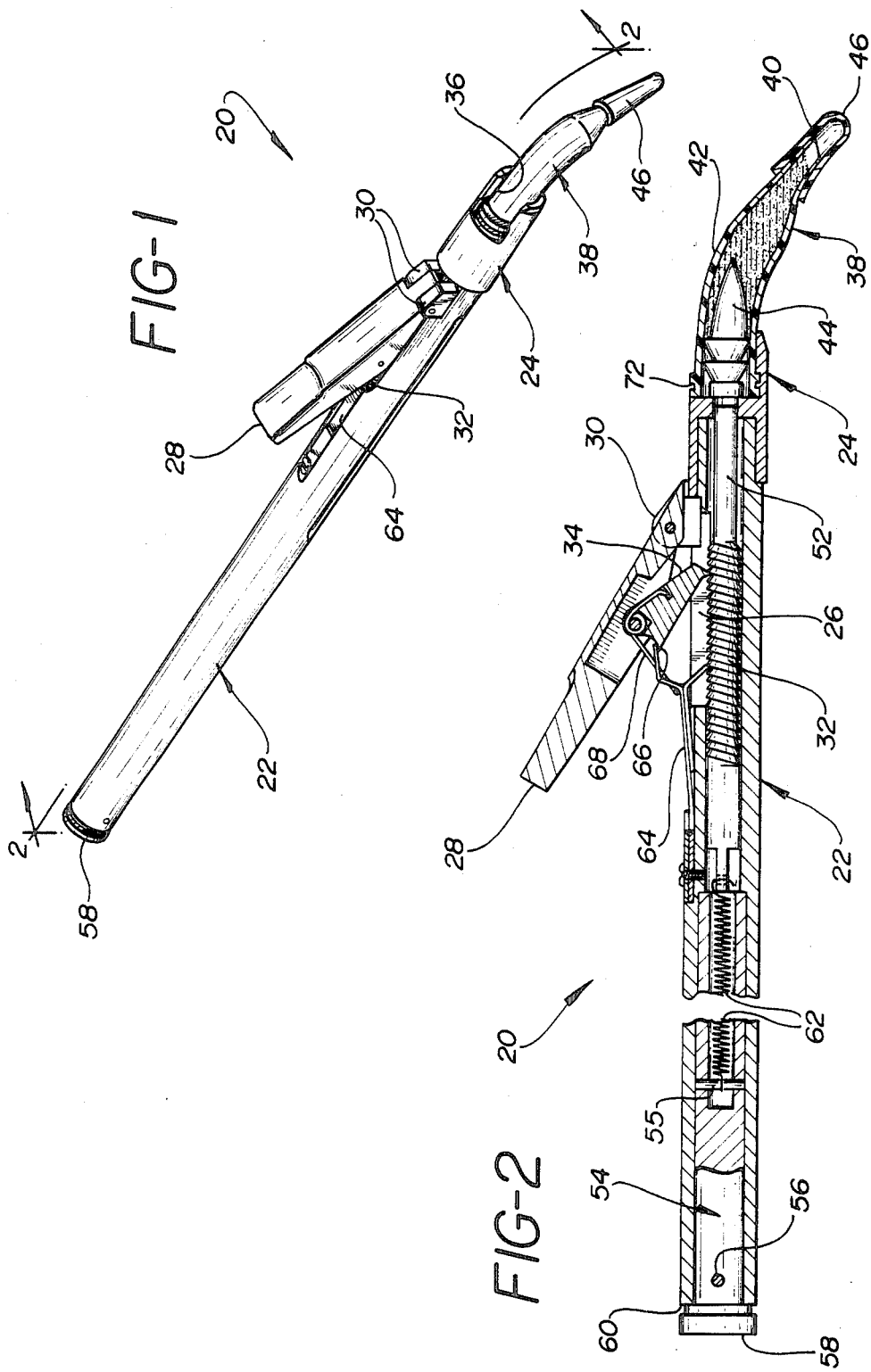

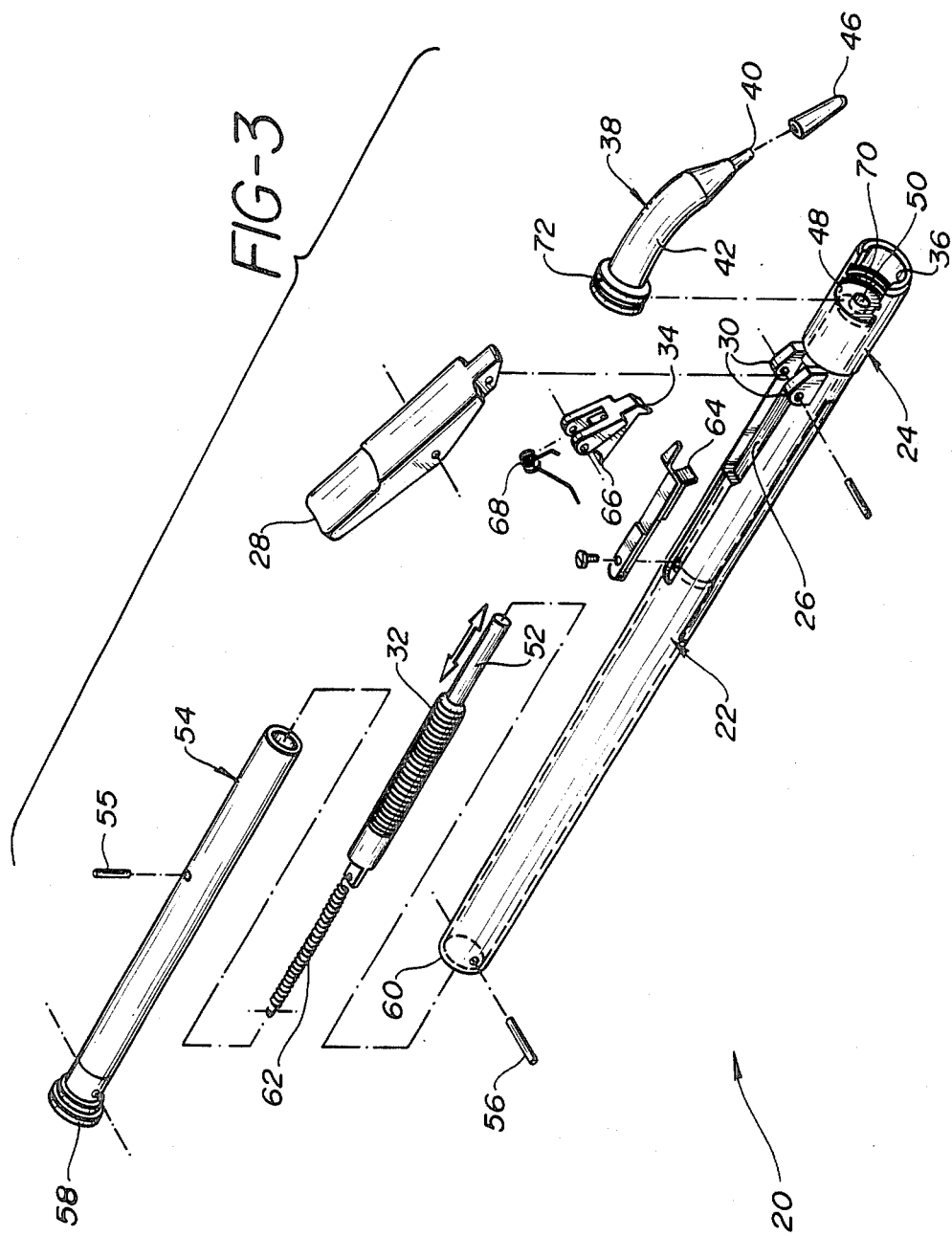

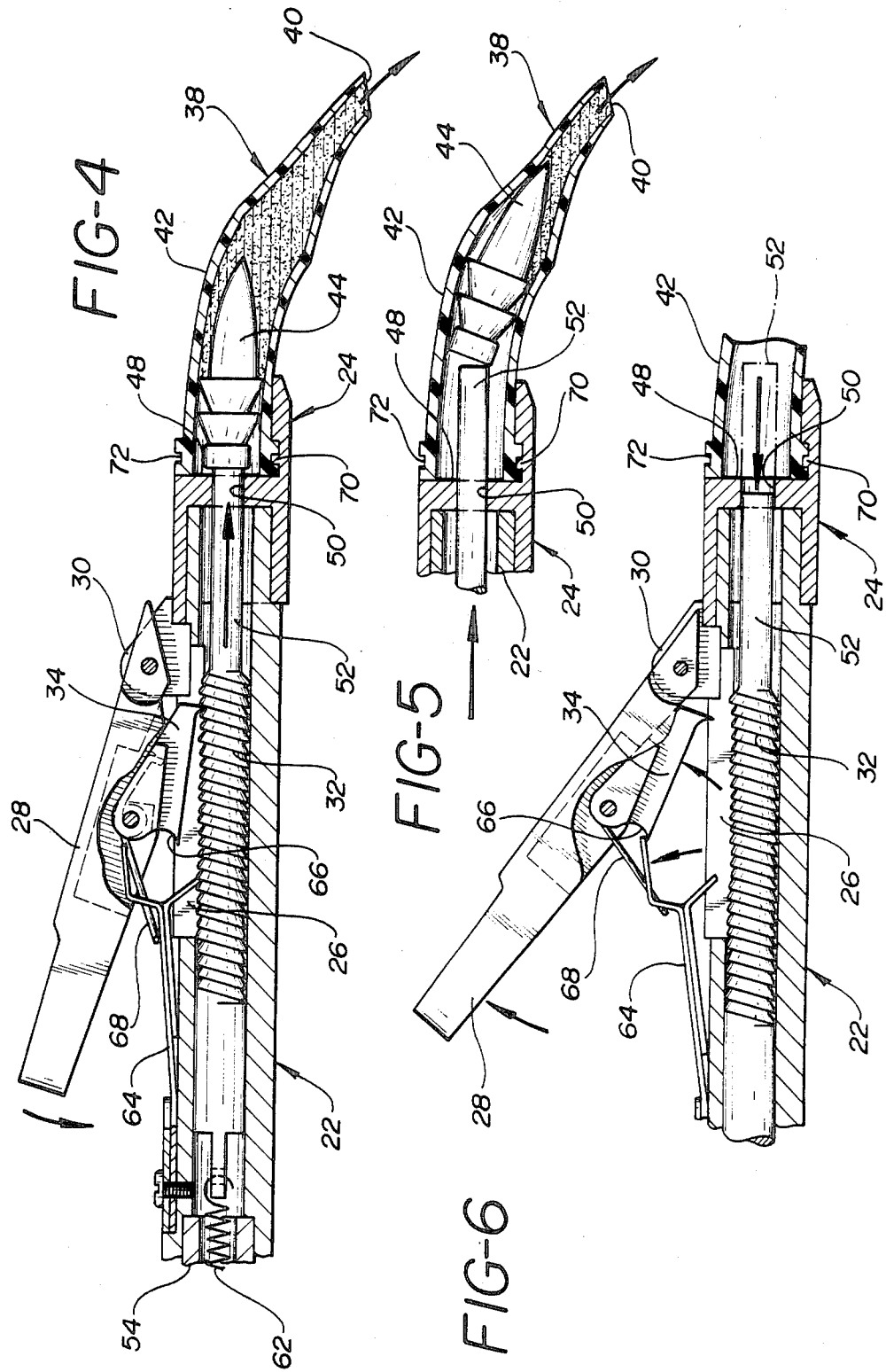

RATCHET TYPE DISPENSER FOR DENTAL MATERIALS

The invention relates to a dispensing device for dental materials which includes a ratchet device.

BACKGROUND OF THE INVENTION

The use of various polymerizable resinous materials is becoming more and more frequent in the dental profession. Such resinous materials are used as pit and fissure sealants to coat the biting surfaces of molars, as sealants to seal the surface of a cavity prior to filling with the dental restorative material, adhesives for orthodontic brackets, crowns, bridges, and the like, and as composites used as dental filling material. In applying these materials, it is desirable to dispense small quantities of the resinous material in a precise location and in precise quantities. This invention is directed to the provision of an instrument that is very useful for accurately dispensing predetermined quantities of paste-like or fluid materials such as dental resins.

BRIEF SUMMARY OF THE INVENTION

The invention provides an applicator for dispensing predetermined quantities of paste-like material or fluid, which comprises, in combination:

a. an elongated hollow housing having a front end and a top surface, said housing including an end wall at the front end, said end wall including a plunger guiding aperture therethrough, and nozzle receiving means in front of said end wall;

b. an opening in said housing in the top surface thereof near the front end thereof, said opening communicating with the interior of the housing;

c. ratchet anchoring means within said housing;

d. ratchet means within said housing operatively attached to said anchoring means by spring means arranged and constructed to urge said ratchet means rearwardly towards a rest position, said ratchet means being accessible through said opening, and said ratchet means including a plunger drive means at the front end thereof positioned to pass through the plunger guiding aperture;

e. lever means positioned over said opening, said lever means being operatively connected to both drive pawl means and detent pawl means such that when the lever means is depressed, the drive pawl means urges the ratchet forward a predetermined distance and when the lever means is elevated, the detent pawl is disengaged, thereby permitting the ratchet means to return to its rest position; and f. nozzle means inserted in said nozzle receiving means, said nozzle means including a front discharge tip and a rear portion comprising a tubular body portion defining a reservoir for paste-like material or fluid, said tubular body portion including an open end at the rear thereof and a piston member therein, said nozzle means being inserted in said nozzle receiving means such that the open end including the position member is aligned with said plunger guiding aperture.

whereby, when said lever is depressed, the ratchet is urged forward thereby forcing the plunger forward through the plunger guiding aperture and the plunger engages the piston and drives it forward to expel a predetermined amount of paste-like material or fluid contained therein out of said reservoir and into said discharge tip, and when said lever is elevated, the plunger withdraws from engagement with the piston and stops forcing the piston forward.

THE PRIOR ART

The following U.S. patents disclose ratchet drive means for dispensers of dental materials as well as other materials:
Hinkel et al., U.S. Pat. No. 3,161,325
Thiel et al., U.S. Pat. No. 3,221,409
Plunger, U.S. Pat. No. 3,640,431
Sartain, U.S. Pat. No. 4,323,176
Vandis et al., U.S. Pat. No. 4,340,367
Paton, U.S. Pat. No. 4,413,760
Lebecque, U.S. Pat. No. 4,440,324
Jacklich, U.S. Pat. No. 4,444,560
Dragan, U.S. Pat. No. 4,472,171.

BRIEF DESCRIPTION OF THE DRAWINGS

FIG. 1 is perspective view of a carrier that embodies the principles of the invention;

FIG. 2 is a longitudinal cross-sectional view taken along line 2—2 of FIG. 1, with the carrier in its normal, rest position;

FIG. 3 is an exploded perspective view of the carrier of FIG. 1;

FIG. 4 is a view similar to FIG. 2, but with the lever depressed showing the related movements of the parts;

FIG. 5 is an enlarged cross-sectional view of the nozzle, showing the piston being moved forward by the plunger; and FIG. 6 is an enlarged cross-sectional view of the ratchet and associated parts, showing the lever in its retracted position and related movements caused thereby.

DETAILED DESCRIPTION OF THE INVENTION

Referring now to the drawings, FIGS. 1-3 show a dispenser 20 that embodies the principles of the invention. The dispenser includes an elongated hollow housing 22 having a nozzle receiver 24 at the front end thereof. Just behind the nozzle receiver 24, and in the top surface of the elongated hollow housing 22, is an elongated opening 26. Mounted above the opening 26 is a lever arm 28. The lever arm 28 is pivotally mounted on a fulcrum 30 that is positioned at the front end of the opening 26. The lever arm is arranged and constructed to engage a ratchet 32 (that is located on the inside of the elongated housing 22) by a drive pawl 34 that is operatively connected to the lever arm 28 as shown in FIGS. 2, 4, and 6.

The nozzle receiver 24 includes a cut-out portion 36 arranged and constructed to receive a nozzle preferably curved 38. The nozzle 38 includes a tip end 40, a tubular reservoir 42, and a piston 44 (see FIGS. 2-5). It is desirable to include a cap 46 to place over the end of the tip 40 to prevent paste-like material or fluid contained in the nozzle 38 from leaking out. The nozzle 38 can be disposable, and can be pre-loaded with a pre-determined quantity of paste-like material or fluid, sufficient for a single or multiple doses. The nozzle 38 can be made of an opaque material (e.g., black pigmented nylon) so that it will be light tight and can therefore be used to contain photopolymerizable resins.

At the rear of the nozzle receiver 24 there is an end wall 48. The rear of the nozzle 38 abuts this end wall 48, as best seen in FIGS. 2, 4, 5, and 6. The end wall contains an aperture 50 therethrough, the purpose of which is to permit a plunger 52 (described below) to pass therethrough and engage the piston 44 to force paste-like material or fluid contained in the nozzle out through the tip end 40 of the nozzle 48.

A ratchet anchoring member 54 is contained within the elongated housing 22 (see FIGS. 2–4). The ratchet anchoring member 54 is fixedly placed within the elongated hollow housing 22 by any convenient means, such as by a pin 56 and a flange 58 that abuts against the rear end 60 of the housing 22. This is best seen in FIGS. 2 and 3. A ratchet spring 62 is fixedly attached within the ratchet anchoring member 54 (as by a pin 55-see FIG. 3) and to the rear of the ratchet 32, as shown in FIG. 3. The ratchet spring 62 tends to urge the ratchet to a rest position within the housing 22, so that at rest the rear end of the ratchet 32 will be abutting the front end of the ratchet anchoring member 54 as is shown in FIG. 2.

In operation, when the lever 28 is depressed, the drive pawl 34 pushes the ratchet 32 forward a predetermined distance, and a detent pawl 64 prevents the ratchet from returning to its rest position. When the ratchet 32 is moved forward, it also moves forward a plunger 52 which passes through the aperture 50 in the end wall 48 located at the front end of the elongated hollow housing 32. When this occurs, the plunger 52 engages the piston 44 located at the rear of the tubular reservoir 42 in the nozzle 48 and forces a predetermined quantity of paste-like material or fluid out of the nozzle 38 through its tip end 40 (See FIGS. 4 and 5). Each time the lever 28 is depressed, the ratchet 32 is moved forward a predetermined distance and causes an additional predetermined quantity of paste-like material or fluid to be forced out of the nozzle 38. When it is desired to return the ratchet to its rest position, the lever 28 is raised, and thereby pulls up the detent pawl 64 by the engaging hook 66 that is located at the rear end of the drive pawl member 34. By thus disengaging the detent pawl, the spring 62 pulls the ratchet 32 back to its rest position adjacent the ratchet anchoring member 54. (See FIG. 6) The detent pawl 64 is a member that is made of a material such as spring steel and is arranged and constructed such that it will normally bear down on to the top of the teeth of the ratchet 32, except when forced upwardly.

The lever spring 68 normally presses the lever arm 28 upwardly to a normal rest position, such as is shown in FIG. 2. When the lever 28 is moved above this rest position, it engages and thereby releases the detent pawl 64; when it is pushed down or depressed below this rest position, it causes the drive pawl 34 to engage the ratchet 32 and push it forward a predetermined distance.

The dispenser of the invention can be made out of any convenient materials, such as machined metal, or the like.

In a preferred embodiment of the invention, the nozzle receiver includes a flange 70 that is made to engage a groove 72 in the rear of the nozzle 38 for tight positioning in the nozzle receiver 24.

The dispenser of the invention is useful for dispensing paste-like materials such as filled resinous materials useful as dental composites, and fluids such as dental pit and fissure sealants.

What is claimed is:

1. An applicator for dispensing predetermined quantities of paste-like material or fluid, which comprises, in combination:
   a. an elongated hollow housing having a longitudinal axis, a front end and a top surface, said housing including an end wall at the front end, said end wall including a plunger guiding aperture therethrough, and nozzle receiving means in front of said end wall;
   b. an opening in said housing in the top of surface thereof near the front end thereof, said opening communicating with the interior of the housing;
   c. ratchet anchoring means within said housing;
   d. ratchet means within said housing operatively attached to said anchoring means by spring means arranged and constructed to urge said ratchet means rearwardly toward a rest position, said ratchet means being accessible through said opening, said ratchet means including a plunger drive means at the front end thereof positioned to pass through the plunger guiding aperture;
   e. a lever means positioned above said opening;
      a drive pawl pivotably connected to said lever means;
      lever spring means for biasing said drive pawl against said lever means;
      detent pawl means fixed to said housing and extending over said opening to engage said ratchet means;
      a portion of said lever spring means resting on said detent pawl means; and
   f. nozzle means inserted in said nozzle receiving means, said nozzle means including a front discharge tip and a rear portion comprising a tubular body portion defining a reservoir for paste-like material or fluid, said tubular body portion including an open end at the rear thereof and a piston member therein, said nozzle means being inserted in said nozzle receiving means such that the open end including the piston member is alinged with said plunger guiding aperture;
   whereby when said lever is depressed, the ratchet is urged forward thereby forcing the plunger forward through the plunger guiding aperture and the plunger engages the piston and drives it forward to expel a predetermined amount of paste-like material or fluid contained therein out of said reservoir and into said discharge tip, and when said lever is elevated, the plunger withdraws from engagement with the piston and stops forcing the piston forward.

2. The applicator of claim 1 further including a hook means extending rearwardly from said drive pawl means and positioned to engage and lift up said detent pawl means when said lever means is lifted.

3. The applicator of claim 1 wherein said nozzle means curves in the direction transversed to said longitudinal axis of said housing and said nozzle means having an interior wall and wherein said piston member is a free piston member unconnected to said plunger drive means and having at least one circumferential flange extending thereabout to maintain contact with said interior wall of said nozzle means.

* * * * *